United States Patent
Zhang et al.

(10) Patent No.: US 11,242,340 B2
(45) Date of Patent: Feb. 8, 2022

(54) CRYSTAL FORMS OF DEMETHYLENEBERBERINE HYDROCHLORIDE AND PREPARATION METHOD THEREFOR

(71) Applicant: China Pharmaceutical University, Jiangsu (CN)

(72) Inventors: Yubin Zhang, Jiangsu (CN); Yuanqiang Zhang, Jiangsu (CN); Miao Zhang, Jiangsu (CN); Qingxia Li, Jiangsu (CN)

(73) Assignee: CHINA PHARMACEUTICAL UNIVERSITY, Jiangsu (CN)

( * ) Notice: Subject to any disclaimer, the term of this patent is extended or adjusted under 35 U.S.C. 154(b) by 44 days.

(21) Appl. No.: 16/960,810

(22) PCT Filed: Jul. 12, 2018

(86) PCT No.: PCT/CN2018/095341
§ 371 (c)(1),
(2) Date: Jul. 8, 2020

(87) PCT Pub. No.: WO2019/153644
PCT Pub. Date: Aug. 15, 2019

(65) Prior Publication Data
US 2020/0392129 A1 Dec. 17, 2020

(30) Foreign Application Priority Data
Feb. 6, 2018 (CN) .......................... 201810115491.2

(51) Int. Cl.
*C07D 455/03* (2006.01)
*A61K 31/4745* (2006.01)
*A61P 9/10* (2006.01)
*A61P 3/06* (2006.01)

(52) U.S. Cl.
CPC ........ *C07D 455/03* (2013.01); *C07B 2200/13* (2013.01)

(58) Field of Classification Search
CPC ..... C07D 455/03; A61K 31/4575; A61P 9/10; A61P 3/06
See application file for complete search history.

(56) References Cited

FOREIGN PATENT DOCUMENTS

| CN | 1827618 A | 9/2006 |
|---|---|---|
| CN | 101153039 A | 4/2008 |
| CN | 102040604 A | 5/2011 |
| CN | 103816152 A | 5/2014 |
| WO | 2009/007457 A2 | 1/2009 |

OTHER PUBLICATIONS

Huo, L., et al., "Synthesis of Rotundine." Chinese Journal of Pharmaceuticals, 2012, 43 (5): 323-325.
Li, Y., et al., "Design, Synthesis, and Cholesterol-Lowering Efficacy for Prodrugs of Berberrubine." Bioorganic & Medicinal Chemistry, 2010, 18: 6422-6428.
Ribaudo, G., et al., "Preliminary Studies of Berberine and its Semi-Synthetic Derivatives as a Promising Class of Multi-Target Anti-Parkinson Agents." National Product Research, 2018, 32 (12): 1395-1401.

*Primary Examiner* — Bruck Kifle
(74) *Attorney, Agent, or Firm* — Saliwanchik, Lloyd & Eisenschenk

(57) ABSTRACT

Provided are four crystal forms, A, B, C and D, of demethyleneberberine hydrochloride, and a preparation method therefor, and further provided are X-ray powder diffraction characteristic absorption peaks, infrared absorption peaks and DSC spectra of the four crystal forms. The X-ray powder diffraction characteristic diffraction peaks of the crystal forms are at about 8.205°, 8.805°, 10.817°, 14.835°, 15.479°, 16.668°, 17.492°, 18.529°, 20.656°, 21.536°, 23.538°, 25.657°, 26.192°, and 28.808°. A preparation method for the four crystal forms of the demethyleneberberine hydrochloride is also involved. The preparation method has a simple process, a high yield and a low cost; and has a high product purity and a stable quality.

8 Claims, 8 Drawing Sheets

CRYSTAL FORMS OF DEMETHYLENEBERBERINE HYDROCHLORIDE AND PREPARATION METHOD THEREFOR

CROSS REFERENCE TO RELATED APPLICATIONS

This application is a National Stage Application of International Application Number PCT/CN2018/095341, filed Jul. 12, 2018; which claims priority to Chinese Application No. 201810115491.2, filed Feb. 6, 2018.

TECHNICAL FIELD

The present invention belongs to the technical field of pharmaceutical chemistry, and particularly relates to four crystal forms of demethyleneberberine hydrochloride and preparation method thereof.

BACKGROUND ART

Demethyleneberberine hydrochloride or demethyleneberberine chloride is represented by a molecular formula of $C_{19}H_{18}NO_4Cl$, and its organic structural portion demethyleneberberine is named as 9,10-dimethoxy-5,6-dihydroisoquinoline[2,1-b]isoquinoline-7-onium-2,3-dihydroxy.

The structural formula of demethyleneberberine hydrochloride is represented by formula (I):

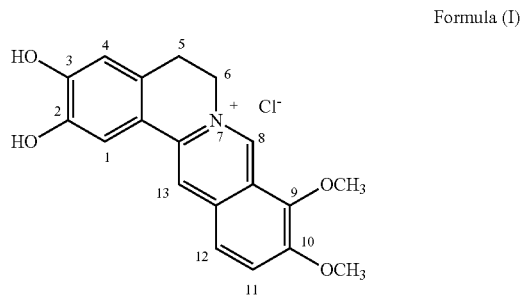

Formula (I)

It is reported that demethyleneberberine hydrochloride has an inhibitory effect on various Gram-positive and Gram-negative bacteria in vitro. Our recent research has demonstrated that demethyleneberberine hydrochloride has certain therapeutic effects on the prevention and treatment of liver fibrosis, acute and chronic alcoholic liver diseases, ulcerative colitis, immune liver injuries and nonalcoholic fatty liver diseases etc. In addition, it is reported in other patent that demethyleneberberine has a good hypoglycemic effect and provides another alternative drug for clinical treatment of diabetes and related diseases.

Demethyleneberberine hydrochloride is found in natural medicinal plants such as phellodendron, *thalictrum*, *Stephania miyiensis*, and the like, and it is also one of the metabolites of berberine hydrochloride in vivo. Demethyleneberberine hydrochloride involves high extraction cost and high price, owing to the low content of demethyleneberberine hydrochloride in natural plants. In our research, pure demethyleneberberine hydrochloride is prepared and obtained from a cheap berberine raw material through chemical synthesis, and thereby the cost is reduced effectively.

In our research, a stable and high-purity demethyleneberberine hydrochloride product is obtained through secondary recrystallization, and the complex subsequent purification process for similar reactions is simplified at the same time. Thus, the yield of demethyleneberberine hydrochloride is greatly improved, and stable crystal forms of demethyleneberberine hydrochloride are obtained. At present, there is no relevant literature or patent reporting the preparation of crystal forms of demethyleneberberine hydrochloride. However, the crystal forms and structures of a drug are extremely important to the stability, dissolution rate and bioavailability of the drug, and appropriate crystal forms of drug are crucial to pharmaceutical research. There are some technical problems in the preparation of stable and high-purity demethyleneberberine hydrochloride in the prior art. Therefore, it is highly necessary to prepare stable and high-purity crystal forms of demethyleneberberine hydrochloride from the perspective of pharmaceutical industrial production.

SUMMARY OF THE INVENTION

The object of the present invention is to provide four crystal forms of demethyleneberberine hydrochloride and preparation method thereof.

A crystal form of demethyleneberberine hydrochloride, designated as crystal form A, characterized in that, it has characteristic diffraction peaks at 6.838, 8.300, 12.477, 13.667, 16.269, 16.642, 17.761, 18.247, 18.749, 20.389, 20.739, 21.926, 22.530, 23.983, 24.819, 25.774, 26.413, 26.592, 28.552, 30.333, and 38.312° in an X-ray powder diffraction spectrum represented by Cu-Kα radiation and 2θ±0.2° diffraction angle; one thermal absorption peak at 240±3° C. in a DSC thermogram; and characteristic infrared absorption peaks at 422.8 $cm^{-1}$, 454.3 $cm^{-1}$, 466.6 $cm^{-1}$, 505.6 $cm^{-1}$, 581.8 $cm^{-1}$, 617.7 $cm^{-1}$, 658.5 $cm^{-1}$, 739.3 $cm^{-1}$, 774.6 $cm^{-1}$, 820.3 $cm^{-1}$, 871.8 $cm^{-1}$, 892.6 $cm^{-1}$, 917.5 $cm^{-1}$, 962.6 $cm^{-1}$, 983.2 $cm^{-1}$, 999.7 $cm^{-1}$, 1,050.0 $cm^{-1}$, 1,067.8 $cm^{-1}$, 1,110.5 $cm^{-1}$, 1,140.5 $cm^{-1}$, 1,203.4 $cm^{-1}$, 1,244.5 $cm^{-1}$, 1,268.1 $cm^{-1}$, 1,293.8 $cm^{-1}$, 1,337.1 $cm^{-1}$, 1,363.8 $cm^{-1}$, 1,390.5 $cm^{-1}$, 1,455.5 $cm^{-1}$, 1,493.9 $cm^{-1}$, 1,515.6 $cm^{-1}$, 1,530.5 $cm^{-1}$, 1,567.1 $cm^{-1}$, 1,605.6 $cm^{-1}$, 1,638.0 $cm^{-1}$, 1,769.6 $cm^{-1}$, 2,726.3 $cm^{-1}$, 2,847.6 $cm^{-1}$, 2,945.2 $cm^{-1}$, 3,024.2 $cm^{-1}$, 3,065.1 $cm^{-1}$, 3,086.0 $cm^{-1}$, and 3,150.6 $cm^{-1}$.

A crystal form of demethyleneberberine hydrochloride, designated as crystal form B, characterized in that, it has characteristic diffraction peaks at 6.838, 8.300, 12.477, 13.667, 16.269, 16.642, 17.761, 18.247, 18.749, 20.389, 20.739, 21.926, 22.530, 23.983, 24.819, 25.774, 26.413, 26.592, 28.552, 30.333, and 38.312° in an X-ray powder diffraction spectrum represented by Cu-Kα radiation and 2θ±0.2° diffraction angle; two thermal absorption peaks at 147±3° C. and 220±3° C. respectively in a DSC thermogram; and characteristic infrared absorption peaks at 421.5 $cm^{-1}$, 448.0 $cm^{-1}$, 464.4 $cm^{-1}$, 506.1 $cm^{-1}$, 523.9 $cm^{-1}$, 543.5 $cm^{-1}$, 568.8 $cm^{-1}$, 583.9 $cm^{-1}$, 618.9 $cm^{-1}$, 649.1 $cm^{-1}$, 676.8 $cm^{-1}$, 718.3 $cm^{-1}$, 742.1 $cm^{-1}$, 777.5 $cm^{-1}$, 833.0 $cm^{-1}$, 859.8 $cm^{-1}$, 878.7 $cm^{-1}$, 924.5 $cm^{-1}$, 960.4 $cm^{-1}$, 977.7 $cm^{-1}$, 1,018.9 $cm^{-1}$, 1,060.0 $cm^{-1}$, 1,107.7 $cm^{-1}$, 1,138.4 $cm^{-1}$, 1,170.1 $cm^{-1}$, 1,207.4 $cm^{-1}$, 1,243.9 $cm^{-1}$, 1,268.6 $cm^{-1}$, 1,366.8 $cm^{-1}$, 1,388.7 $cm^{-1}$, 1,422.7 $cm^{-1}$, 1,445.5 $cm^{-1}$, 1,457.3 $cm^{-1}$, 1,492.8 $cm^{-1}$, 1,517.8 $cm^{-1}$, 1,533.9 $cm^{-1}$, 1,568.8 $cm^{-1}$, 1,610.9 $cm^{-1}$, 1,636.9 $cm^{-1}$, 1,735.5 $cm^{-1}$, 2,646.6 $cm^{-1}$, 2,849.8 $cm^{-1}$, 2,952.5 $cm^{-1}$, 2,993.5 $cm^{-1}$, 3,089.6 $cm^{-1}$, and 3,364.3 $cm^{-1}$.

A crystal faun of demethyleneberberine hydrochloride, designated as crystal form C, characterized in that, it has characteristic diffraction peaks at 3.260, 8.515, 9.715, 12.147, 13.219, 14.789, 17.607, 18.306, 20.728, 21.261, 24.633, 25.430, 25.837, 26.416, 27.606, 28.147, and 37.695° in an X-ray powder diffraction spectrum represented by Cu-Kα radiation and 2θ±0.2° diffraction angle; one thermal absorption peak at 253±3° C. in a DSC thermogram; and characteristic infrared absorption peaks at 422.8 cm$^{-1}$, 441.6 cm$^{-1}$, 452.2 cm$^{-1}$, 505.0 cm$^{-1}$, 526.2 cm$^{-1}$, 584.6 cm$^{-1}$, 637.3 cm$^{-1}$, 652.0 cm$^{1}$, 665.7 cm$^{-1}$, 699.9 cm$^{-1}$, 723.4 cm$^{-1}$, 742.0 cm$^{-1}$, 774.1 cm$^{-1}$, 814.2 cm$^{-1}$, 828.2 cm$^{-1}$, 869.6 cm$^{-1}$, 891.7 cm$^{1}$, 915.6 cm$^{-1}$, 964.5 cm$^{-1}$, 980.6 cm$^{-1}$, 998.8 cm$^{-1}$, 1,065.8 cm$^{-1}$, 1,108.5 cm$^{-1}$, 1,139.7 cm$^{-1}$, 1,192.2 cm$^{-1}$, 1,216.5 cm$^{-1}$, 1,241.0 cm$^{-1}$, 1,273.9 cm$^{-1}$, 1,287.4 cm$^{-1}$, 1,308.2 cm$^{-1}$, 1,343.5 cm$^{-1}$, 1,356.5 cm$^{-1}$, 1,389.3 cm$^{-1}$, 1,420.2 cm$^{-1}$, 1,437.9 cm$^{-1}$, 1,456.1 cm$^{-1}$, 1,510.2 cm$^{-1}$, 1,565.5 cm$^{-1}$, 1,580.9 cm$^{-1}$, 1,604.3 cm$^{-1}$, 1,618.6 cm$^{-1}$, 1,633.2 cm$^{-1}$, 2,697.9 cm$^{-1}$, 2,842.7 cm$^{-1}$, 2,946.1 cm$^{-1}$, 3,005.3 cm$^{-1}$, and 3,066.4 cm$^{-1}$.

A crystal form of demethyleneberberine hydrochloride, designated as crystal form D, characterized in that, it has characteristic diffraction peaks at about 6.034, 8.699, 12.589, 18.108, 21.854, 24.224, 25.146 and 26.172° in an X-ray powder diffraction spectrum represented by Cu-Kα radiation and 2θ diffraction angle; two thermal absorption peaks at 131±3° C. and 190±3° C. respectively in a DSC thermogram; and characteristic infrared absorption peaks at 422.8 cm$^{-1}$, 454.3 cm$^{-1}$, 466.6 cm$^{-1}$, 505.6 cm$^{-1}$, 581.8 cm$^{-1}$, 617.7 cm$^{-1}$, 658.5 cm$^{-1}$, 739.3 cm$^{-1}$, 774.6 cm$^{-1}$, 820.3 cm$^{-1}$, 871.8 cm$^{-1}$, 892.6 cm$^{-1}$, 917.5 cm$^{-1}$, 962.6 cm$^{-1}$, 983.2 cm$^{-1}$, 999.7 cm$^{-1}$, 1,050.0 cm$^{-1}$, 1,067.8 cm$^{-1}$, 1,110.5 cm$^{-1}$, 1,140.5 cm$^{-1}$, 1,203.4 cm$^{-1}$, 1,244.5 cm$^{-1}$, 1,268.1 cm$^{-1}$, 1,293.8 cm$^{-1}$, 1,337.1 cm$^{-1}$, 1,363.8 cm$^{-1}$, 1,390.5 cm$^{-1}$, 1,455.5 cm$^{-1}$, 1,493.9 cm$^{-1}$, 1,515.6 cm$^{1}$, 1,530.5 cm$^{-1}$, 1,567.1 cm$^{-1}$, 1,605.6 cm$^{-1}$, 1,638.0 cm$^{-1}$, 1,769.6 cm$^{-1}$, 2,726.3 cm$^{-1}$, 2,847.6 cm$^{-1}$, 2,945.2 cm$^{-1}$, 3,024.2 cm$^{-1}$, 3,065.1 cm$^{-1}$, 3,086.0 cm$^{-1}$, and 3,150.6 cm$^{1}$.

A method for preparing the crystal forms of demethyleneberberine hydrochloride, comprising the following steps:

(1) adding 4 g of phloroglucinol into 100 ml of 40%-60% sulfuric acid, and stirring, so that the phloroglucinol is dissolved;

(2) adding 5 g of berberine hydrochloride into the solution obtained in the step (1), and stirring for 2 h at 80° C.-100° C.;

(3) adding the solution obtained in the step (2) into 100 ml of saturated salt solution, and stirring for 2 h;

(4) filtering the mixed solution obtained in the step (3) by suction-filtration, dissolving the filter cake with 100 ml of methanol in water bath at 70° C., and recrystallizing;

(5) filtering the solution obtained in the step (4) by suction-filtration, dissolving the filter cake with 100 ml of methanol in water bath at 70° C., recrystallizing, and performing suction-filtration;

(6) drying the yellow solid obtained in the step (5) by vacuum drying for 24 h at room temperature, so that a crystal form B of demethyleneberberine hydrochloride is obtained;

(7) filtering the solution obtained in the step (4) by suction-filtration, dissolving the filter cake with 100 ml of ethanol in water bath at 80° C., recrystallizing, and performing suction-filtration;

(8) drying the yellow solid obtained in the step (7) by vacuum drying for 24 h at room temperature, so that a crystal form C of demethyleneberberine hydrochloride is obtained;

(9) filtering the solution obtained in the step (4) by suction-filtration, dissolving 1 g of filter cake with 12 ml of ethanol in water bath at 80° C. while stirring, performing suction-filtration and collecting the filter cake;

(10) drying the yellow solid obtained in the step (9) by vacuum drying for 24 h at room temperature, so that a crystal form A of demethyleneberberine hydrochloride is obtained;

(11) filtering the solution obtained in the step (4) by suction-filtration, dissolving 1 g of filter cake with 30 ml of deionized water in water bath at 74° C. while stirring, recrystallizing, and performing suction-filtration;

(12) drying the yellow solid obtained in the step (11) by vacuum freeze-drying for 48 h, so that a crystal form D of demethyleneberberine hydrochloride is obtained.

In the preparation method of the crystal forms of demethyleneberberine hydrochloride, the step (5) further comprises: adding a small amount of seed crystals, adding 10-20 vol. % of diethyl ether, adding 10-20 vol. % of xylene, and adding 10-20 vol. % of toluene.

In the preparation method of the crystal forms of demethyleneberberine hydrochloride, the step (7) further comprises: adding a small amount of seed crystals, adding 10-20 vol. % of diethyl ether, adding 10-20 vol. % of xylene, and adding 10-20 vol. % of toluene.

The crystal forms A, B, C and D of demethyleneberberine hydrochloride, are used to form pharmaceutical composition, the pharmaceutical composition may be tablets, capsules, pills, injections, sustained-release agents, and various microparticle administration systems. The four crystal forms of demethyleneberberine hydrochloride provided by the present invention are yellow powder in appearance.

The preparation method of the crystal forms of demethyleneberberine hydrochloride provided by the present invention comprises the following main steps: first, phloroglucinol is added into a sulfuric acid system and subjected to stirring for dissolution, then berberine hydrochloride is added into the solution and subjected to stirring. After certain time of reaction, the reaction solution is mixed with saturated salt solution, and the mixture is stirred and suction-filtered to obtain a filter cake. Then the filter cake is dissolved in methanol and subjected to crystallization, and the crystallization solution is suction-filtered to obtain a crude demethyleneberberine hydrochloride product. The crude product is dissolved in methanol and subjected to crystallization, or a small amount of seed crystals or toluene, diethyl ether and xylene are added into methanol or ethanol solution and the product is subjected to crystallization, suction-filtration and drying, so that a crystal form B of demethyleneberberine hydrochloride is obtained. The crude product is dissolved in ethanol and subjected to crystallization, or a small amount of seed crystals or toluene, diethyl ether and xylene are added into methanol or ethanol solution and the product is subjected to crystallization, suction-filtration and drying, so that a crystal faint C of demethyleneberberine hydrochloride is obtained. The crude product is washed with a small amount of ethanol under heating, the filter cake is filtered and collected, so that a crystal form A of demethyleneberberine hydrochloride is obtained. The crude product is dissolved in an appropriate amount of deionized water and subjected to crystallization, suction-filtration and drying, so that a crystal faun D of demethyleneberberine hydrochloride is obtained. Through HPLC analysis, it is verified that the purity values of the four crystal forms of demethyleneberberine hydrochloride are greater than 99%; through NMR and MS detections, it is verified that the structure is correct. By comparing the solubility of the four crystal forms of demethyleneberberine hydrochloride, it is found that the solubility of the crystal form C is the highest, while the solubility of the crystal form D is the lowest.

The demethyleneberberine hydrochloride of the present invention may be used for the preparation of drugs for treating liver fibrosis, acute and chronic alcoholic liver diseases, ulcerative colitis, immune liver injuries and non-alcoholic fatty liver diseases.

The pharmaceutical compositions comprising the four crystal forms of demethyleneberberine hydrochloride may be tablets, capsules, pills, injections, sustained-release agents and various microparticle administration systems.

Beneficial Technical Effects of the Present Invention

In terms of crystal forms, products in different crystal forms may be obtained with different preparation methods, such as different recrystallization methods. There is no regularity in the preparation of crystal forms. Different crystal forms may be produced simply by altering certain crystallization conditions. The stability, solubility and in-vivo pharmacokinetic parameters of drugs in different crystal forms are generally different. Special attention is paid to the protection of new crystal forms in new drug researches or patent applications. Up to now, a large number of patent applications for drugs in different crystal forms have been granted, which fully proves that crystal form protection is the focus of attention of those skilled in the art.

The preparation method of different crystal forms of demethyleneberberine hydrochloride provided by the present invention is simple, achieves high yield and good product quality, and involves low cost. However, the four crystal forms have obvious differences in terms of pharmaceutical properties. Under stability test conditions such as high temperature, high humidity and strong light irradiation, crystal forms A, B and C of demethyleneberberine hydrochloride are stable, while crystal form D tends to have crystal transformation under conditions such as high temperature and strong light irradiation. In addition, solubility in water, methanol and ethanol systems of the four crystal forms of demethyleneberberine hydrochloride are compared, and the research result shows: solubility of crystal form C of demethyleneberberine hydrochloride>solubility of crystal form B of demethyleneberberine hydrochloride>solubility of crystal form A of demethyleneberberine hydrochloride>solubility of crystal form D of demethyleneberberine hydrochloride. It is found in in-vivo pharmacokinetic research that: for crystal form A of demethyleneberberine hydrochloride, $C_{max}$=0.292 µg×ml$^{-1}$, $t_{max}$=2 h; for crystal form B of demethyleneberberine hydrochloride, $C_{max}$=0.642 µg×ml$^{-1}$, $t_{max}$=1 h; for crystal form C of demethyleneberberine hydrochloride, $C_{max}$=1.262 µg×ml$^{-1}$, $t_{max}$=0.5 h; for crystal form D of demethyleneberberine hydrochloride, $C_{max}$=1.234 µg×ml$^{-1}$, $t_{max}$=2 h. Through calculation on the basis of the experimental results, it is found that AUC of crystal form D=3.675 µg×ml$^{-1}$×h>AUC of crystal form A=1.247 µg×ml$^{-1}$×h>AUC of crystal form B=1.150 µg×ml$^{-1}$×h>AUC of crystal form C=1.077 µg×ml$^{-1}$×h. Though no pharmacodynamic data of different crystal forms is provided in the present invention, the pharmacokinetic parameters of different crystal forms, such as $C_{max}$, $t_{1/2}$ and AUC parameters, are tested, and these parameters can excellently reflect the effective concentration, onset time, drug potency, etc. of the drug when playing its therapeutic effect in vivo. It is found in our research that these pharmacokinetic parameters of the four different crystal forms of demethyleneberberine hydrochloride are significantly different, indicating that different crystal forms of demethyleneberberine hydrochloride have different therapeutic effects in vivo.

EMBODIMENTS

The following examples can help those skilled in the art to understand the present invention more comprehensively, without constituting any limitation to the present invention in any way.

X-ray powder diffraction, differential scanning calorimetry and infrared spectrum are used for structural characterization of the crystal forms of demethyleneberberine hydrochloride in the present invention.

Figure 1:
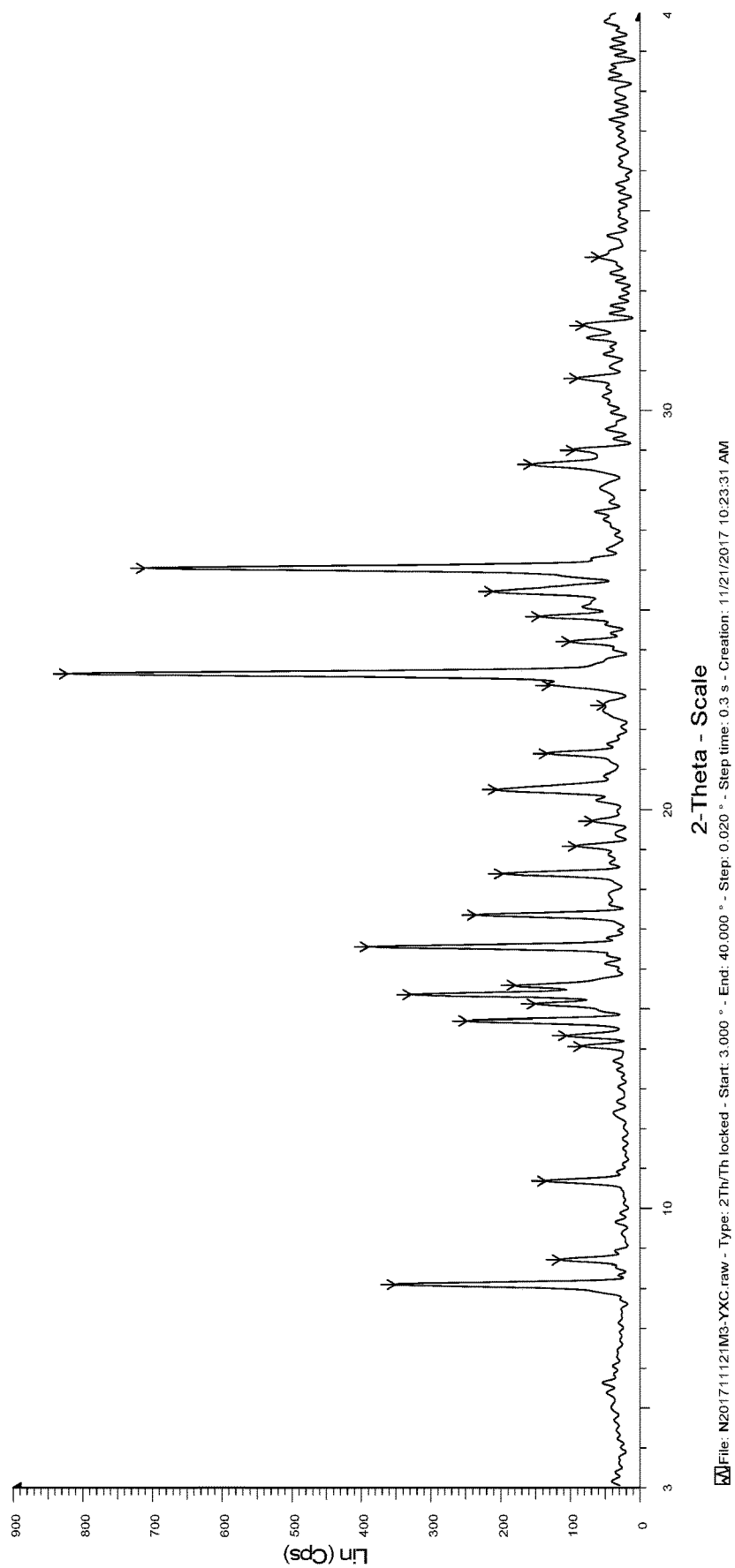
FIG. 1 shows an X-ray powder diffraction pattern of the crystal form A of demethyleneberberine hydrochloride according to the present invention.
Figure 2:
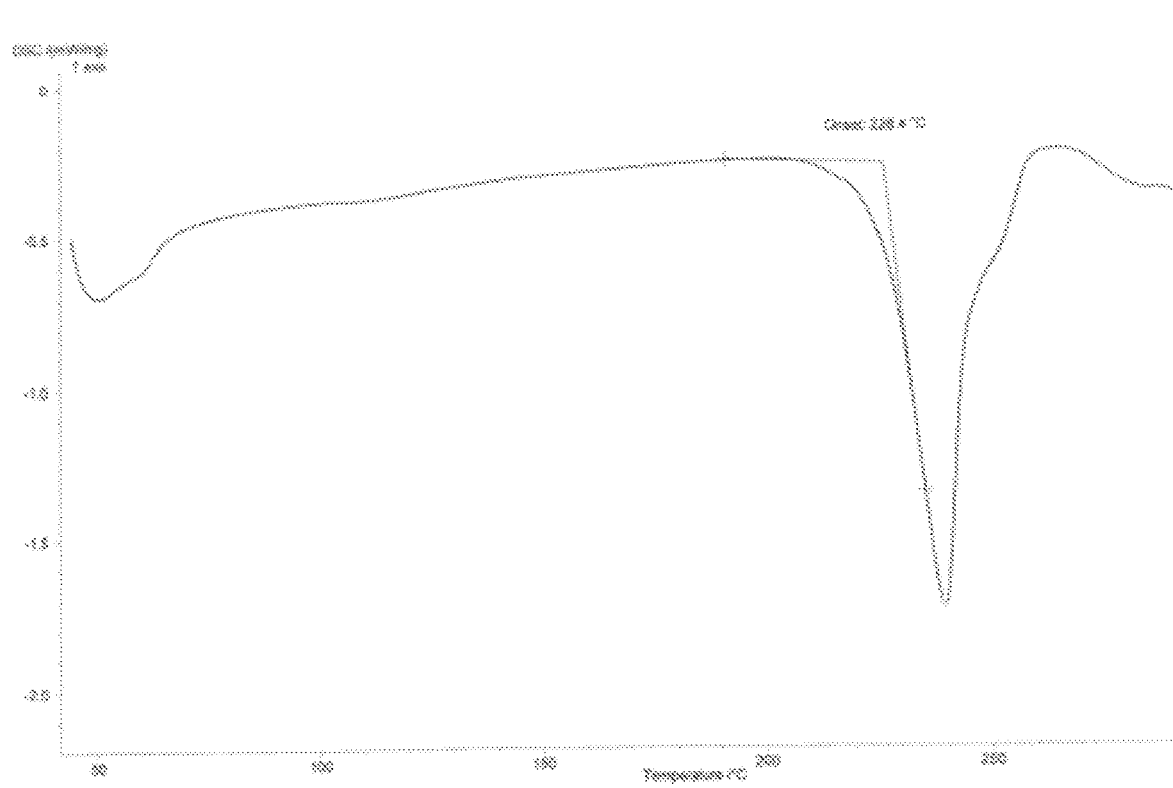
FIG. 2 shows a differential scanning calorimetry (DSC) thermogram of the compound in FIG. 1.
Figure 3:
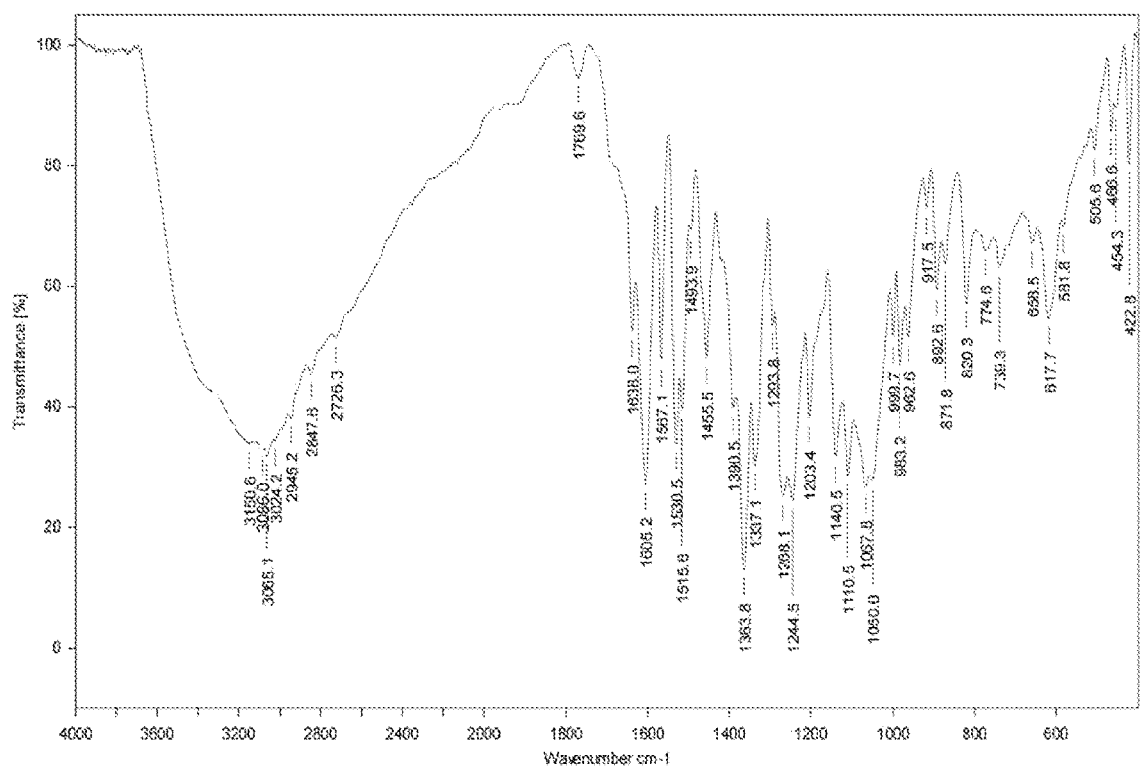
FIG. 3 shows an infrared spectrum of the compound in FIG. 1.

Example 1. Synthesis of Crystal Form a of Demethyleneberberine Hydrochloride 5 g of phloroglucinol is added into 100 ml of 60% $H_2SO_4$ system at 90° C. and stirred to dissolve fully; 6 g of berberine hydrochloride is added; under the catalysis of phloroglucinol, the reaction is held for 2 h, so that methylene is removed and demethyleneberberine hydrochloride is obtained. After the reaction is completed, the reaction solution is poured into 100 ml of saturated salt solution and the mixture is stirred for 2 h. The solution is suction-filtered and a filter cake is obtained; 100 ml of methanol is added into the filter cake, and the filter cake is dissolved fully in water bath at 70° C., the solution is placed in a beaker for recrystallization, or a small amount of xylene or toluene or diethyl ether is added for recrystallization utilizing the mixed solvent. The crystallization solution obtained in the previous step is suction-filtered, and the filter cake is collected and weighed. 1 g of filter cake is taken and added into 12 ml of ethanol, the mixture is placed in water bath at 80° C. and stirred for 20 min., and then is suction-filtered; the filter cake is collected and dried, so that a crystal form A of demethyleneberberine hydrochloride is obtained; then the product is weighed and tested. An X-ray powder diffraction diagram of the obtained solid is shown in FIG. 1, a DSC thermogram is shown in FIG. 2, and an infrared spectrum is shown in FIG. 3.

Figure 4:
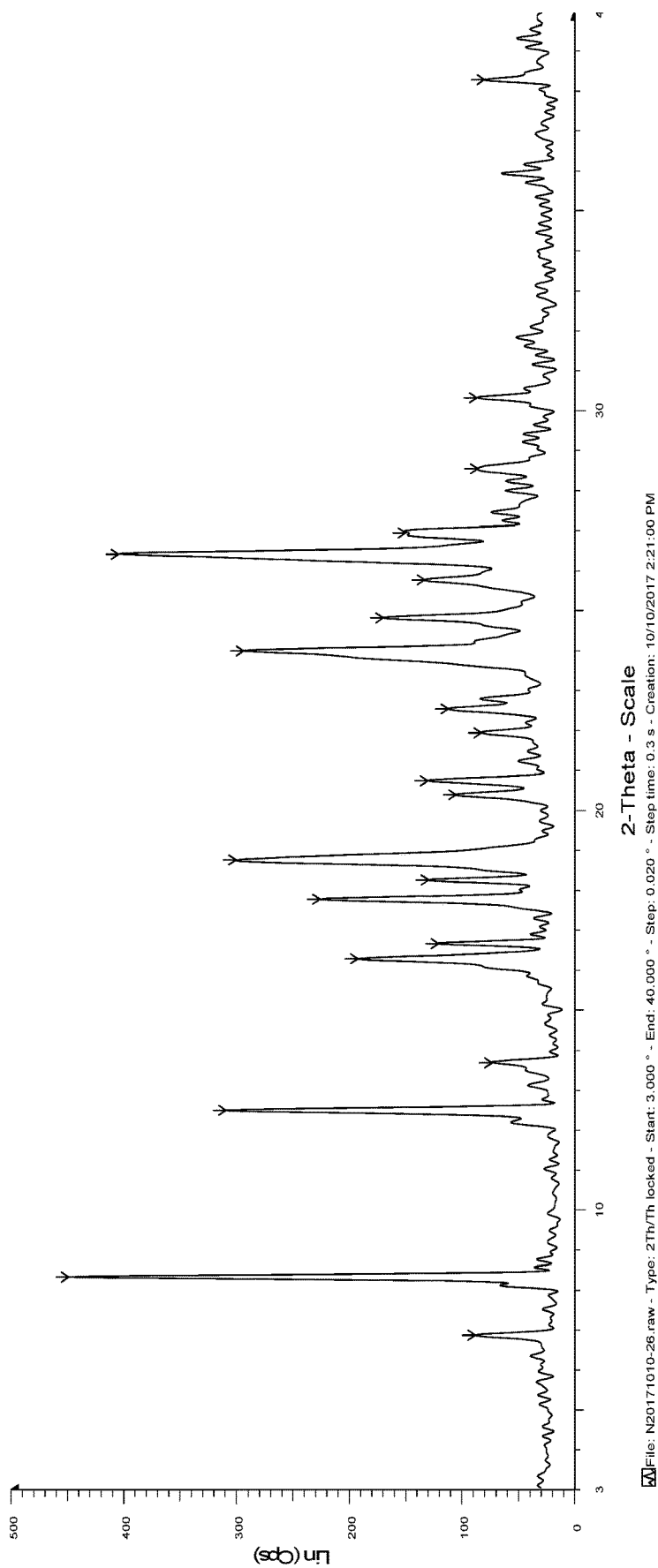
FIG. 4 shows an X-ray powder diffraction pattern of the crystal form B of demethyleneberberine hydrochloride according to the present invention.
Figure 5:
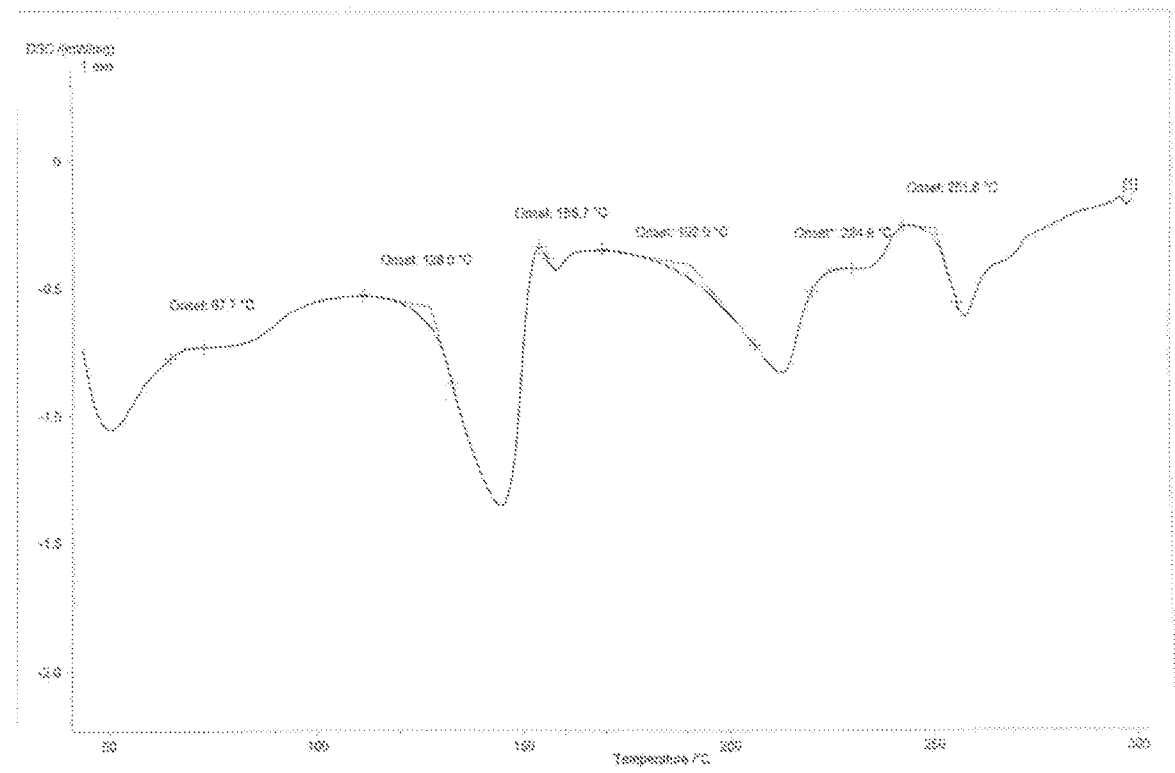
FIG. 5 shows a differential scanning calorimetry (DSC) thermogram of the compound in FIG. 4.
Figure 6:
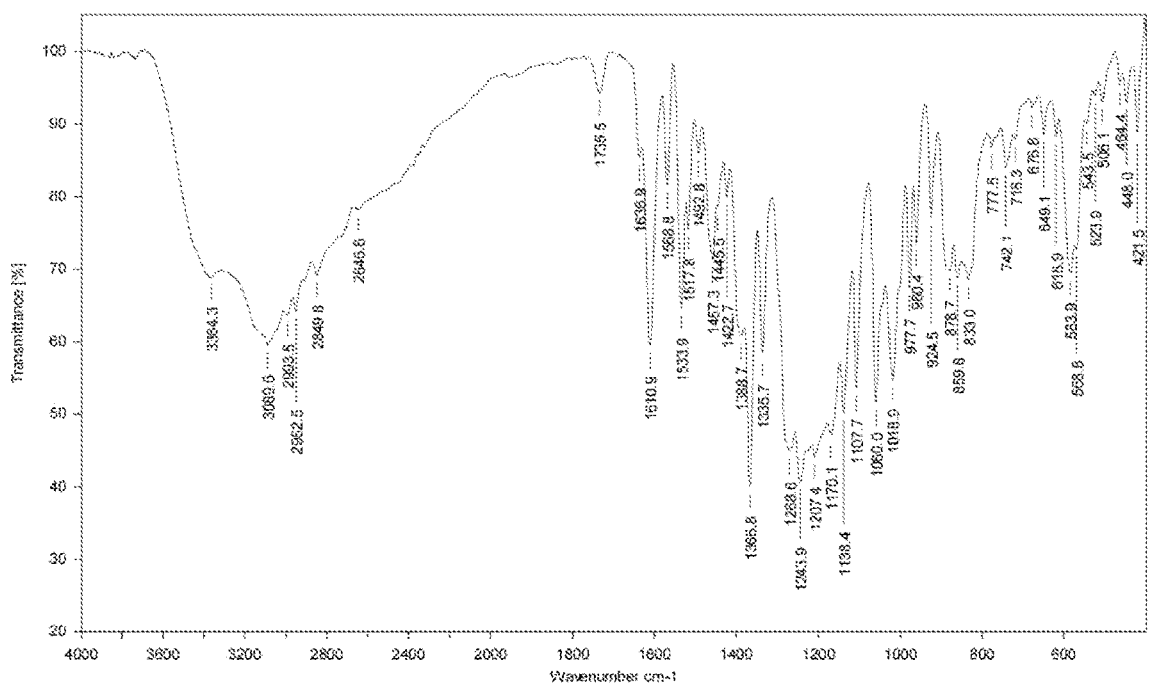
FIG. 6 shows an infrared spectrum of the compound in FIG. 4.

Example 2. Synthesis of Crystal Form B od Demethyleneberberine Hydrochloride 5 g of phloroglucinol is added into 100 ml of 60% $H_2SO_4$ system at 90° C. and stirred to dissolve fully; 6 g of berberine hydrochloride is added; under the catalysis of phloroglucinol, the reaction is held for 2 h, so that methylene is removed and demethyleneberberine hydrochloride is obtained. After the reaction is completed, the reaction solution is poured into 100 ml of saturated salt solution and the mixture is stirred for 2 h for exchange. The solution is suction-filtered and a filter cake is obtained; 100 ml of methanol is added, the filter cake is dissolved fully in water bath at 70° C., the solution is placed in a beaker for recrystallization, or a small amount of xylene or toluene or diethyl ether is added for recrystallization utilizing the mixed solvent. The crystallization solution obtained in the previous step is suction-filtered, and the filter cake is collected and weighed. 70 ml of methanol is added, and the filter cake is dissolved fully in water bath at 70° C.; the solution is placed in a beaker, and recrystallization is carried out at room temperature, utilizing a single-component solvent; or a small amount of xylene or toluene or diethyl ether is added, and recrystallization is carried out, utilizing a mixed solvent, so that a crystal form B of demethyleneberberine hydrochloride is obtained. The product is suction-filtered, dried, weighed and tested. An X-ray powder diffraction pattern of the obtained solid is shown in FIG. 4, a DSC thermogram is shown in FIG. 5, and an infrared spectrum is shown in FIG. 6.

Figure 7:
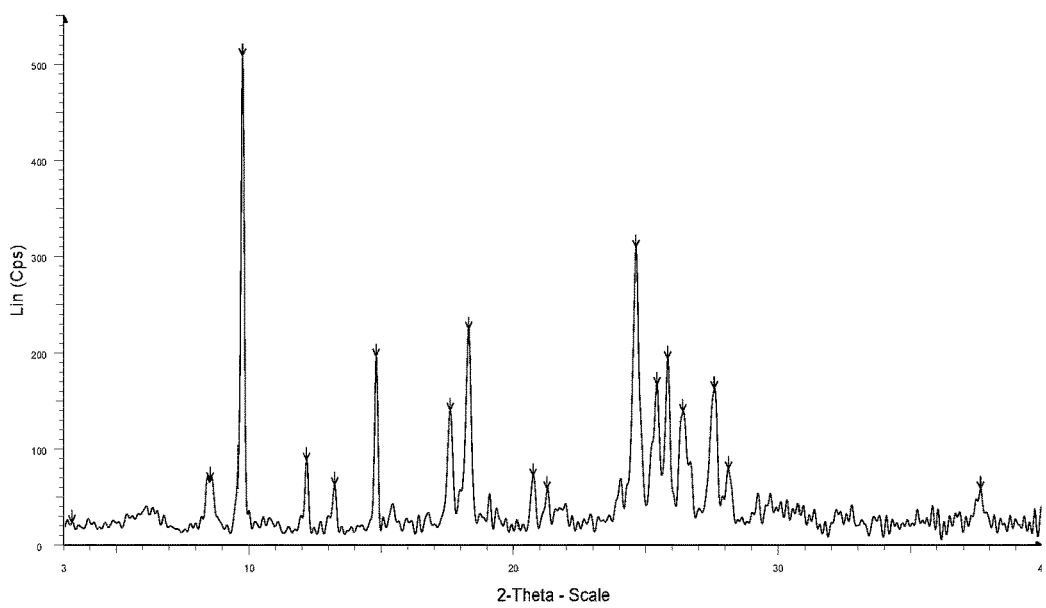
FIG. 7 shows an X-ray powder diffraction pattern of the crystal form C of demethyleneberberine hydrochloride according to the present invention.
Figure 8:
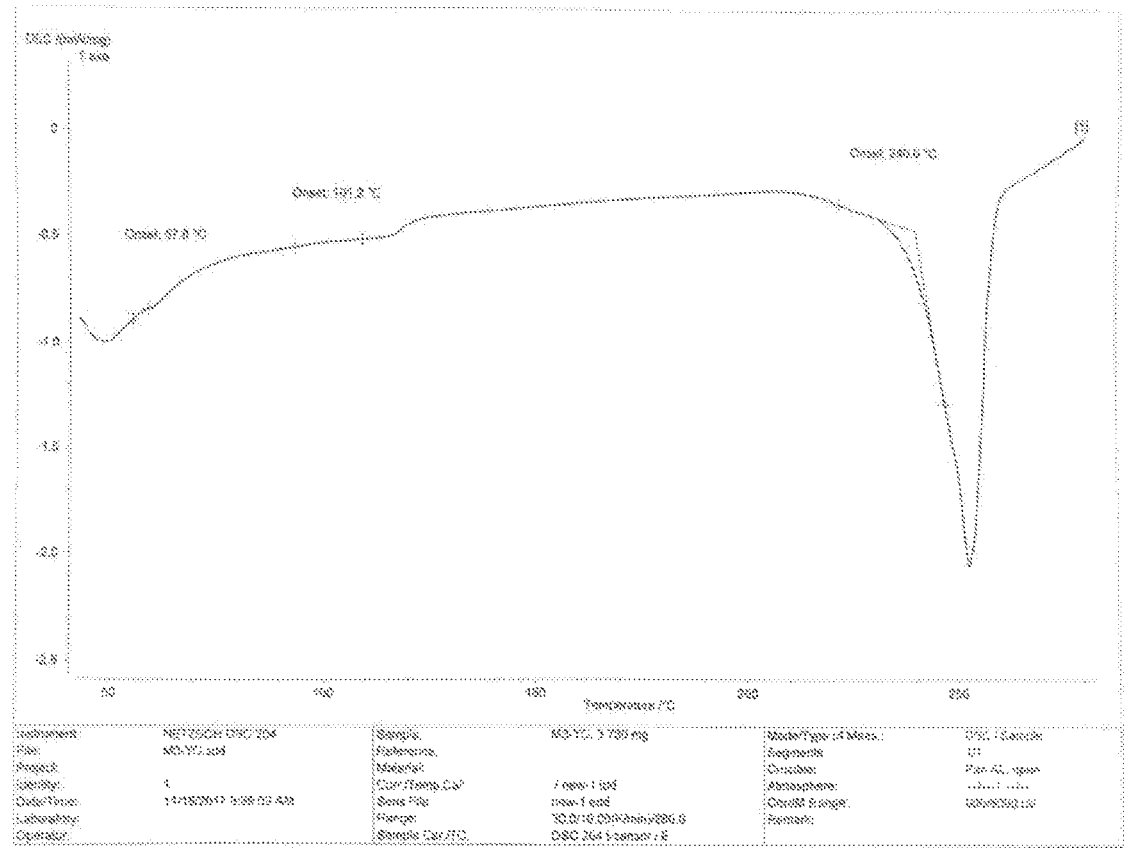
FIG. 8 shows a differential scanning calorimetry (DSC) thermogram of the compound in FIG. 7.
Figure 9:
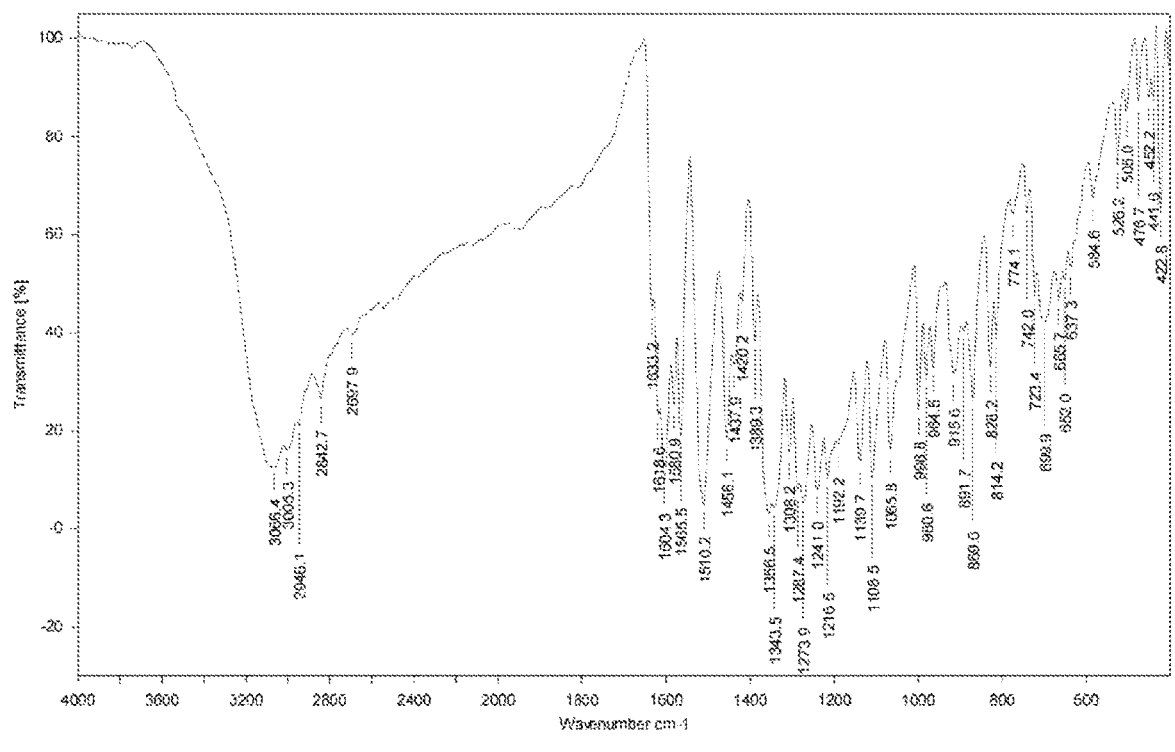
FIG. 9 shows an infrared spectrum of the compound in FIG. 7.

Example 3. Synthesis of Crystal Form C of Demethyleneberberine Hydrochloride 5 g of phloroglucinol is added into 100 ml of 60% $H_2SO_4$ system at 90° C. and stirred to dissolve fully; 6 g of berberine hydrochloride is added; under the catalysis of phloroglucinol, the reaction is held for 2 h, so that methylene is removed and demethyleneberberine hydrochloride is obtained. After the reaction is completed, the reaction solution is poured into 100 ml of saturated salt solution and the mixture is stirred for 2 h. The solution is suction-filtered and a filter cake is obtained; 100 ml of methanol is added to the filter cake, and the filter cake is dissolved fully in water bath at 70° C., the solution is placed in a beaker for recrystallization, or a small amount of xylene or toluene or diethyl ether is added for recrystallization utilizing the mixed solvent. The crystallization solution obtained in the previous step is suction-filtered, and the filter cake is collected and weighed. 120 ml of ethanol is added, and the filter cake is dissolved fully in water bath at 80° C.; the solution is placed in a beaker, and recrystallization is carried out overnight at 4° C.; then the product is suction-filtered and dried, so that a crystal form C of demethyleneberberine hydrochloride is obtained; then the obtained product is weighed and tested. An X-ray powder diffraction pattern of the obtained solid is shown in FIG. 7, a DSC thermogram is shown in FIG. 8, and an infrared spectrum is shown in FIG. 9.

Figure 10:
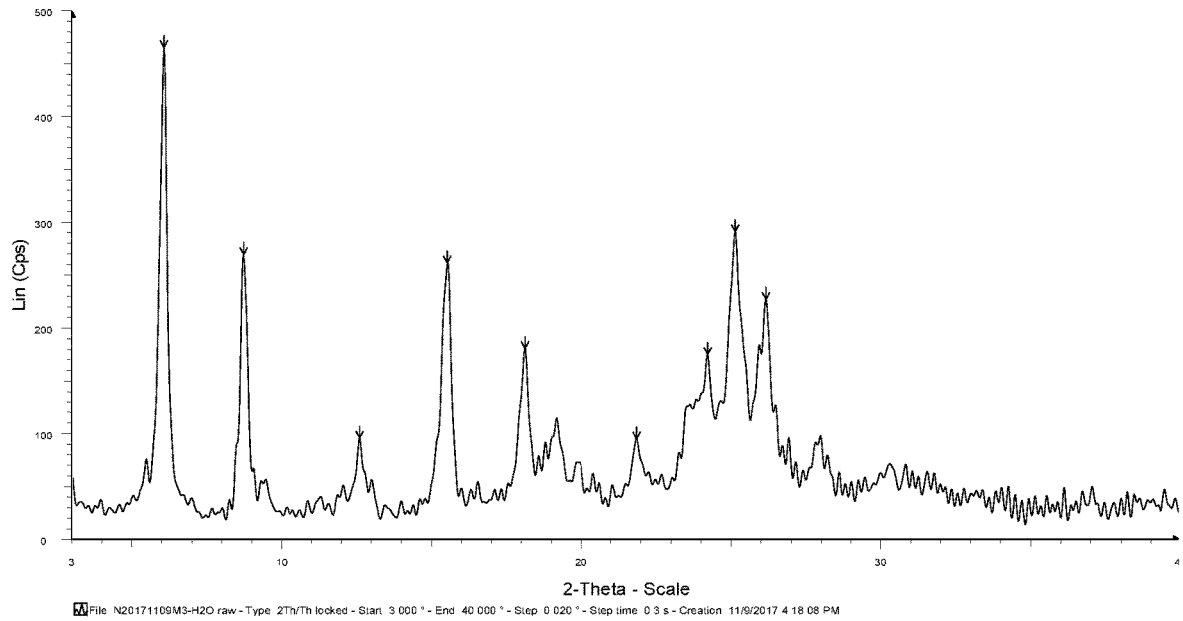
FIG. 10 shows an X-ray powder diffraction pattern of the crystal form D of demethyleneberberine hydrochloride according to the present invention.
Figure 11:
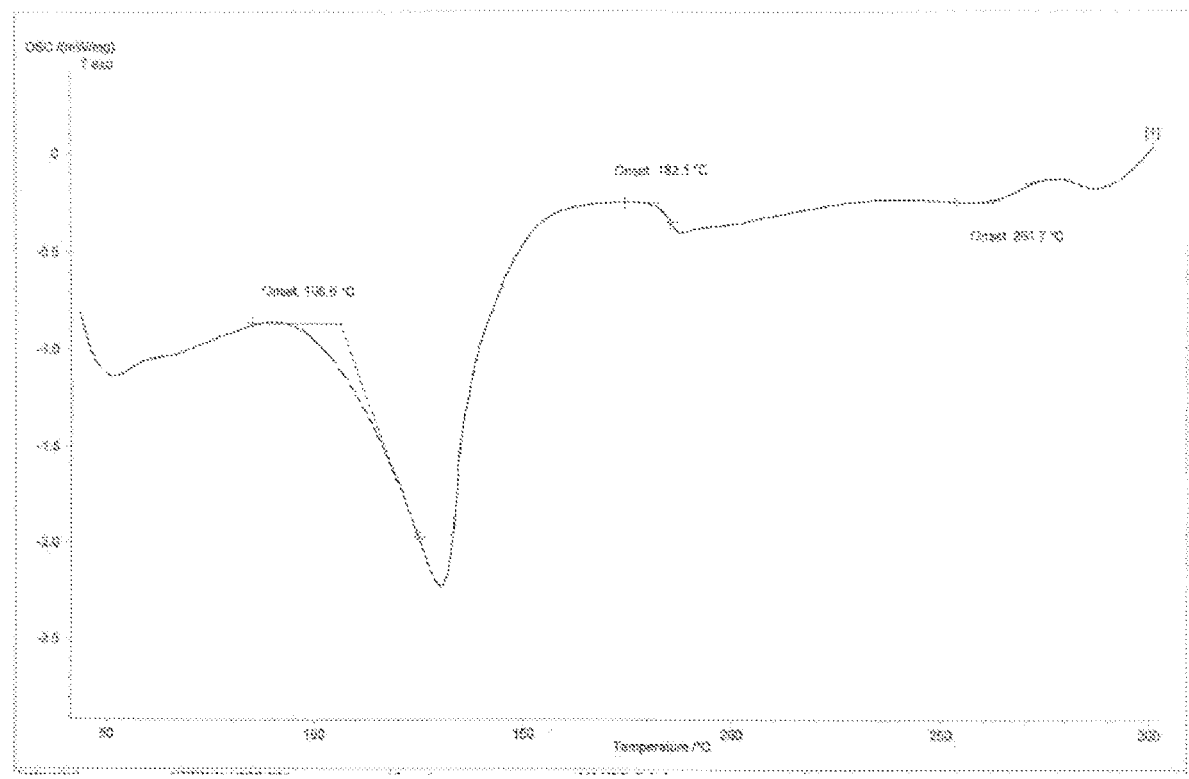
FIG. 11 shows a differential scanning calorimetry (DSC) thermogram of the compound in FIG. 10.
Figure 12:
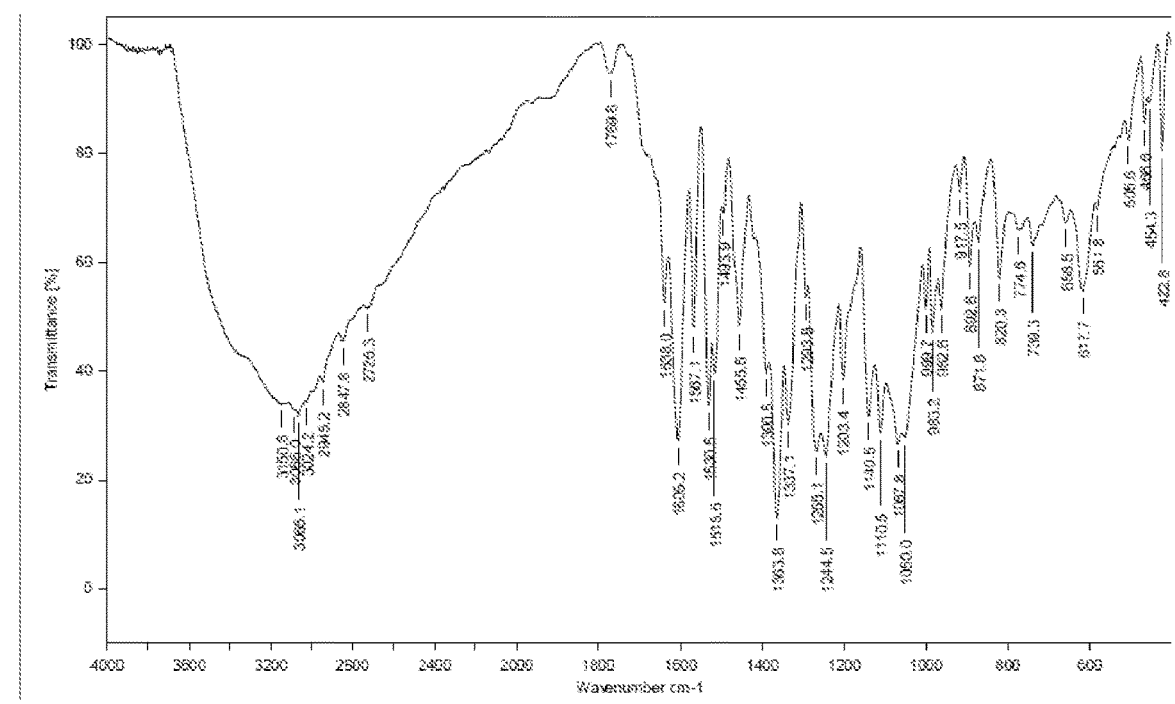
FIG. 12 shows an infrared spectrum of the compound in FIG. 10.

Example 4. Synthesis of Crystal Form D of Demethyleneberberine Hydrochloride 5 g of phloroglucinol is added into 100 ml of 60% $H_2SO_4$ system at 90° C. and stirred to dissolve fully; 6 g of berberine hydrochloride is added; under the catalysis of phloroglucinol, the reaction is held for 2 h, so that methylene is removed and demethyleneberberine hydrochloride is obtained. After the reaction is completed, the reactant solution is poured into 100 ml of saturated salt solution and the mixture is stirred for 2 h. The solution is suction-filtered, and the filter cake is collected; 100 ml of methanol is added, and the filter cake is dissolved fully in water bath at 70° C.; then the solution is placed in a beaker and recrystallization is carried out. The crystallization solution obtained in the previous step is suction-filtered, the filter cake is collected and weighed; thus, a crude product of demethyleneberberine hydrochloride is obtained. 1 g of crude product is taken, 30 ml of deionized water is added to the crude product, and the crude product is dissolved fully in water bath at 74° C.; the solution is placed in a beaker, and recrystallization is carried out at room temperature; then the solution is suction-filtered, and the obtained product is vacuum freeze-dried; thus, a crystal form D of demethyleneberberine hydrochloride is obtained; then the obtained product is weighed and tested. An X-ray powder diffraction pattern of the obtained solid is shown in FIG. 10, a DSC thermogram is shown in FIG. 11, and an infrared spectrum is shown in FIG. 12.

Example 5. Study on Stability of Demethyleneberberine Hydrochloride Crystals in High-Temperature Experiment Demethyleneberberine hydrochloride crystals A, B, C and D are taken in an appropriate amount and placed in plates numbered as A1, B1, C1 and D1 respectively, and then the plates are placed in a high-temperature environment at 60±2° C. respectively for stability test. The experimental results are shown as follows. The demethyleneberberine hydrochloride crystals A, B and C are relatively stable in the high-temperature environment, while the demethyleneberberine hydrochloride crystal D is unstable in the long-term high-temperature environment, and undergoes crystal transformation.

| Sample No. | Test Time (day) | Content (%) | Content of Relevant Substance (%) | X-Ray Powder Diffraction |
|---|---|---|---|---|
| A1 | 0 | 99.62 | 0.38 | Unchanged |
|  | 5 | 99.63 | 0.37 | Unchanged |
|  | 10 | 99.61 | 0.39 | Unchanged |
| B1 | 0 | 99.82 | 0.18 | Unchanged |
|  | 5 | 99.62 | 0.38 | Unchanged |
|  | 10 | 99.67 | 0.33 | Unchanged |
| C1 | 0 | 99.18 | 0.82 | Unchanged |
|  | 5 | 99.21 | 0.79 | Unchanged |
|  | 10 | 99.19 | 0.81 | Unchanged |
| D1 | 0 | 99.78 | 0.22 | Unchanged |
|  | 5 | 99.83 | 0.17 | Unchanged |
|  | 10 | 99.71 | 0.29 | Changed |

Example 6. Study on Stability of Demethyleneberberine Hydrochloride Crystals in High-Humidity Experiment Demethyleneberberine hydrochloride crystals A, B, C and D are taken in an appropriate amount and placed in plates numbered as A2, B2, C2 and D2 respectively, and then the plates are placed in a high-humidity environment at RH90±5% respectively for stability test. The experimental results are shown in the following table. The demethyleneberberine hydrochloride crystals A, B, C and D are relatively stable in the high-humidity environment.

| Sample No. | Test Time (day) | Content (%) | Content of Relevant Substance (%) | X-Ray Powder Diffraction |
|---|---|---|---|---|
| A2 | 0 | 99.62 | 0.38 | Unchanged |
|  | 5 | 99.58 | 0.42 | Unchanged |
|  | 10 | 99.60 | 0.40 | Unchanged |
| B2 | 0 | 99.58 | 0.42 | Unchanged |
|  | 5 | 99.60 | 0.40 | Unchanged |
|  | 10 | 99.56 | 0.44 | Unchanged |
| C2 | 0 | 99.77 | 0.23 | Unchanged |
|  | 5 | 99.72 | 0.28 | Unchanged |
|  | 10 | 99.57 | 0.43 | Unchanged |
| D2 | 0 | 99.48 | 0.52 | Unchanged |
|  | 5 | 99.41 | 0.59 | Unchanged |
|  | 10 | 99.32 | 0.68 | Unchanged |

Example 7. Study on Stability of Demethyleneberberine Hydrochloride Crystals in Strong Light Irradiation Experiment Demethyleneberberine hydrochloride crystals A, B, C and D are taken in an appropriate amount and placed in plates numbered as A3, B3, C3 and D3 respectively, and then the plates are placed in a strong light irradiation environment at 4,500 lx±500 lx respectively for stability test. The experimental results are shown in the following table. The demethyleneberberine hydrochloride crystals A, B and C are relatively stable in the strong light irradiation environment, while the demethyleneberberine hydrochloride crystal D is unstable in the long-term strong light irradiation environment, and undergoes crystal transformation.

| Sample No. | Test Time (day) | Content (%) | Content of Relevant Substance (%) | X-Ray Powder Diffraction |
|---|---|---|---|---|
| A3 | 0 | 99.62 | 0.38 | Unchanged |
|  | 5 | 99.61 | 0.39 | Unchanged |
|  | 10 | 99.60 | 0.40 | Unchanged |
| B3 | 0 | 99.58 | 0.42 | Unchanged |
|  | 5 | 99.77 | 0.23 | Unchanged |
|  | 10 | 99.67 | 0.33 | Unchanged |
| C3 | 0 | 99.57 | 0.43 | Unchanged |
|  | 5 | 99.49 | 0.51 | Unchanged |
|  | 10 | 99.55 | 0.45 | Unchanged |
| D3 | 0 | 99.78 | 0.22 | Unchanged |
|  | 5 | 99.58 | 0.42 | Unchanged |
|  | 10 | 99.64 | 0.36 | Changed |

Figure 13:
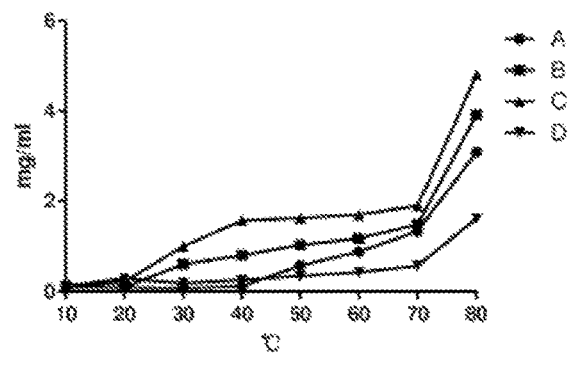
FIG. 13 shows solubility curves of the compounds in FIGS. 1, 4, 7 and 10 in water system.

Example 8. Study on Solubility of Demethyleneberberine Hydrochloride Crystals A, B, C and D in Water System Demethyleneberberine hydrochloride crystals A, B, C and D are taken in an appropriate amount and the solubility of demethyleneberberine hydrochloride crystals A, B, C and D at different temperatures in a water system is studied respectively. 20 µl of sample is taken at each temperature node and detected by HPLC. The experimental results are shown in FIG. 13. Solubility of crystal form C of demethyleneberberine hydrochloride>solubility of crystal form B of demethyleneberberine hydrochloride>solubility of crystal form A of demethyleneberberine hydrochloride>solubility of crystal form D of demethyleneberberine hydrochloride.

Figure 14:
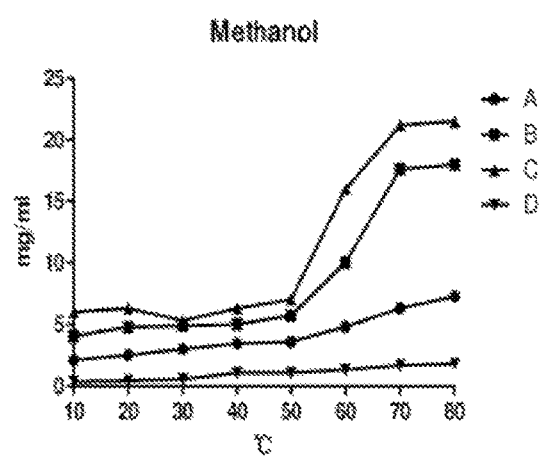
FIG. 14 shows solubility curves of the compounds in FIGS. 1, 4, 7 and 10 in methanol system.

Example 9. Study on Solubility of Demethyleneberberine Hydrochloride Crystals A, B, C and D in Methanol System Demethyleneberberine hydrochloride crystals A, B, C and D are taken in an appropriate amount and the solubility of demethyleneberberine hydrochloride crystals A, B, C and D at different temperatures in a methanol system is studied respectively. 20 µl of sample is taken at each temperature node and detected by HPLC. The experimental results are shown in FIG. 14. Solubility of crystal form C of demethyleneberberine hydrochloride>solubility of crystal form B of demethyleneberberine hydrochloride>solubility of crystal form A of demethyleneberberine hydrochloride>solubility of crystal form D of demethyleneberberine hydrochloride.

Figure 15:
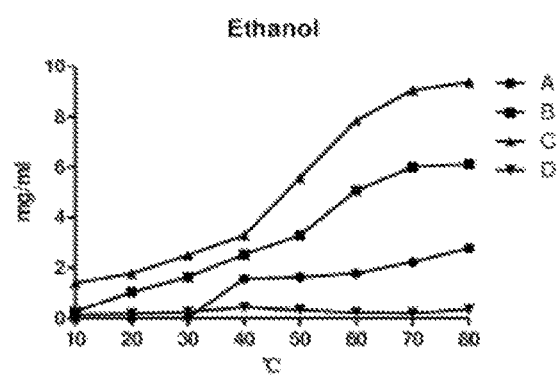
FIG. 15 shows solubility curves of the compounds in FIGS. 1, 4, 7 and 10 in ethanol system.

Example 10. Study on Solubility of Demethyleneberberine Hydrochloride Crystals A, B, C and D in Ethanol System Demethyleneberberine hydrochloride crystals A, B, C and D are taken in an appropriate amount and the solubility of demethyleneberberine hydrochloride crystals A, B, C and D at different temperatures in an ethanol system is studied respectively. 20 µl of sample is taken at each temperature node and detected by HPLC. The experimental results are shown in FIG. 15. Solubility of crystal form C of demethyleneberberine hydrochloride>solubility of crystal form B of demethyleneberberine hydrochloride>solubility of crystal form A of demethyleneberberine hydrochloride>solubility of crystal form D of demethyleneberberine hydrochloride.

Figure 16:
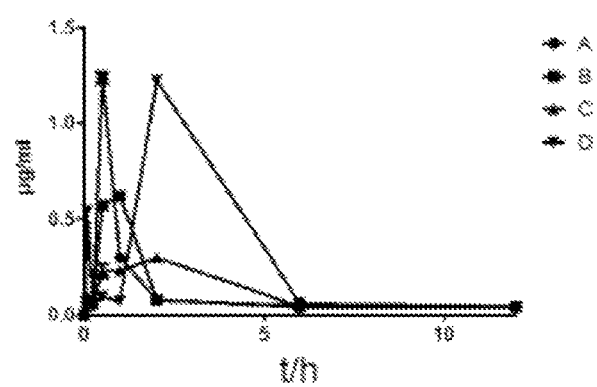
FIG. 16 shows blood concentration and time curves of the compounds in FIGS. 1, 4,7 and 10.

Example 11. Determination of Blood Concentration of Demethyleneberberine Hydrochloride Crystals A, B, C and D Male SD rats are adaptively bred for 3 days, and rats having (220±20) g body weight are selected and divided into 5 groups, namely, blank group, demethyleneberberine hydrochloride crystal form A group, demethyleneberberine hydrochloride crystal form B group, demethyleneberberine hydrochloride crystal form C group and demethyleneberberine hydrochloride crystal form D group. Food supply is stopped for 12 h for gastric emptying before the experiment. For the rats in the experimental groups, ig (intragastric) administration dosage is 200 mg/kg. 0.2 ml of blood is taken from the orbits of the rats at 5 min., 15 min., 30 min., 1 h, 2 h, 6 h and 12 h respectively after ig administration, the whole blood is centrifuged, and 100 µl of plasma is taken and frozen at −20° C. for use later. 100 µl of plasma sample is taken, 200 µl of methanol is added into the plasma sample, the mixture is vortexed for 5 min., and then centrifuged at 10,000 r/min. for 15 min. in a centrifuge; the supernatant is taken and tested by HPLC. The experimental results are shown in FIG. 16. For crystal form A of demethyleneberberine hydrochloride, $C_{max}=0.292$ µg×ml$^{-1}$, $t_{max}=2$ h; for crystal form B of demethyleneberberine hydrochloride, $C_{max}=0.642$ µg×ml$^{-1}$, $t_{max}=1$ h; for crystal form C of demethyleneberberine hydrochloride, $C_{max}$=1.262 µg×ml$^{-1}$, $t_{max}$=0.5 h; for crystal form D of demethyleneberberine hydrochloride, $C_{max}$=1.234 µg×ml$^{-1}$, $t_{max}$=2 h. Through calculation on the basis of the experimental results, it is determined: $D_{AUC}$=3.675 µg×ml$^{-1}$×h>$A_{AUC}$=1.247 µg×ml$^{-1}$×h>$B_{AUC}$=1.150 µg×ml$^{-1}$×h>$C_{AUC}$=1.077 µg×ml$^{-1}$×h.

The invention claimed is:

1. A crystal form of demethyleneberberine hydrochloride selected from:
   A) a crystal form designated as crystal form A, characterized in that, it has characteristic diffraction peaks at 6.838, 8.300, 12.477, 13.667, 16.269, 16.642, 17.761, 18.247, 18.749, 20.389, 20.739, 21.926, 22.530, 23.983, 24.819, 25.774, 26.413, 26.592, 28.552, 30.333, and 38.312° in an X-ray powder diffraction spectrum represented by Cu-Kα radiation and 2θ±0.2° diffraction angle; one thermal absorption peak at 240±3° C. in a DSC thermogram; and characteristic infrared absorption peaks at 422.8 cm$^{-1}$, 454.3 cm$^{-1}$, 466.6 cm$^{-1}$, 505.6 cm$^{-1}$, 581.8 cm$^{-1}$, 617.7 cm$^{-1}$, 658.5 cm$^{-1}$, 739.3 cm$^{-1}$, 774.6 cm$^{-1}$, 820.3 cm$^{-1}$, 871.8 cm$^{-1}$, 892.6 cm$^{-1}$, 917.5 cm$^{-1}$, 962.6 cm$^{-1}$, 983.2 cm$^{-1}$, 999.7 cm$^{-1}$, 1,050.0 cm$^{-1}$, 1,067.8 cm$^{-1}$, 1,110.5 cm$^{-1}$, 1,140.5 cm$^{-1}$, 1,203.4 cm$^{-1}$, 1,244.5 cm$^{-1}$, 1,268.1 cm$^{-1}$, 1,293.8 cm$^{-1}$, 1,337.1 cm$^{-1}$, 1,363.8 cm$^{-1}$, 1,390.5 cm$^{-1}$, 1,455.5 cm$^{-1}$, 1,493.9 cm$^{-1}$, 1,515.6 cm$^{-1}$, 1,530.5 cm$^{-1}$, 1,567.1 cm$^{-1}$, 1,605.6 cm$^{-1}$, 1,638.0 cm$^{-1}$, 1,769.6 cm$^{-1}$, 2,726.3 cm$^{-1}$, 2,847.6 cm$^{-1}$, 2,945.2 cm$^{-1}$, 3,024.2 cm$^{-1}$, 3,065.1 cm$^{-1}$, 3,086.0 cm$^{-1}$, and 3,150.6 cm$^{-1}$;
   B) crystal form designated as crystal form B, characterized in that, it has characteristic diffraction peaks at 6.838, 8.300, 12.477, 13.667, 16.269, 16.642, 17.761, 18.247, 18.749, 20.389, 20.739, 21.926, 22.530, 23.983, 24.819, 25.774, 26.413, 26.592, 28.552, 30.333, and 38.312° in an X-ray powder diffraction spectrum represented by Cu-Kα radiation and 2θ±0.2° diffraction angle; two thermal absorption peaks at 147±3° C. and 220±3° C. respectively in a DSC thermogram; and characteristic infrared absorption peaks at 421.5 cm$^{-1}$, 448.0 cm$^{-1}$, 464.4 cm$^{-1}$, 506.1 cm$^{-1}$, 523.9 cm$^{-1}$, 543.5 cm$^{-1}$, 568.8 cm$^{-1}$, 583.9 cm$^{-1}$, 618.9 cm$^{-1}$, 649.1 cm$^{-1}$, 676.8 cm$^{-1}$, 718.3 cm$^{-1}$, 742.1 cm$^{-1}$, 777.5 cm$^{-1}$, 833.0 cm$^{-1}$, 859.8 cm$^{-1}$, 878.7 cm$^{-1}$, 924.5 cm$^{-1}$, 960.4 cm$^{-1}$, 977.7 cm$^{-1}$, 1,018.9 cm$^{-1}$, 1,060.0 cm$^{-1}$, 1,107.7 cm$^{-1}$, 1,138.4 cm$^{-1}$, 1,170.1 cm$^{-1}$, 1,207.4 cm$^{-1}$, 1,243.9 cm$^{-1}$, 1,268.6 cm$^{-1}$, 1,366.8 cm$^{-1}$, 1,388.7 cm$^{-1}$, 1,422.7 cm$^{-1}$, 1,445.5 cm$^{-1}$, 1,457.3 cm$^{-1}$, 1,492.8 cm$^{-1}$, 1,517.8 cm$^{-1}$, 1,533.9 cm$^{-1}$, 1,568.8 cm$^{-1}$, 1,610.9 cm$^{-1}$, 1,636.9 cm$^{-1}$, 1,735.5 cm$^{-1}$, 2,646.6 cm$^{-1}$, 2,849.8 cm$^{-1}$, 2,952.5 cm$^{-1}$, 2,993.5 cm$^{-1}$, 3,089.6 cm$^{-1}$, and 3,364.3 cm$^{-1}$;
   C) a crystal form designated as crystal form C, characterized in that, it has characteristic diffraction peaks at 3.260, 8.515, 9.715, 12.147, 13.219, 14.789, 17.607, 18.306, 20.728, 21.261, 24.633, 25.430, 25.837, 26.416, 27.606, 28.147, and 37.695° in an X-ray powder diffraction spectrum represented by Cu-Kα radiation and 2θ±0.2° diffraction angle; one thermal absorption peak at 253±3° C. in a DSC thermogram; and characteristic infrared absorption peaks at 422.8 cm$^{-1}$, 441.6 cm$^{-1}$, 452.2 cm$^{-1}$, 505.0 cm$^{-1}$, 526.2 cm$^{-1}$, 584.6 cm$^{-1}$, 637.3 cm$^{-1}$, 652.0 cm$^{-1}$, 665.7 cm$^{-1}$, 699.9 cm$^{-1}$, 723.4 cm$^{-1}$, 742.0 cm$^{-1}$, 774.1 cm$^{-1}$, 814.2 cm$^{-1}$, 828.2 cm$^{-1}$, 869.6 cm$^{-1}$, 891.7 cm$^{-1}$, 915.6 cm$^{-1}$, 964.5 cm$^{-1}$, 980.6 cm$^{-1}$, 998.8 cm$^{-1}$, 1,065.8 cm$^{-1}$, 1,108.5 cm$^{-1}$, 1,139.7 cm$^{-1}$, 1,192.2 cm$^{-1}$, 1,216.5 cm$^{-1}$, 1,241.0 cm$^{-1}$, 1,273.9 cm$^{-1}$, 1,287.4 cm$^{-1}$, 1,308.2 cm$^{-1}$, 1,343.5 cm$^{-1}$, 1,356.5 cm$^{-1}$, 1,389.3 cm$^{-1}$, 1,420.2 cm$^{-1}$, 1,437.9 cm$^{-1}$, 1,456.1 cm$^{-1}$, 1,510.2 cm$^{-1}$, 1,565.5 cm$^{-1}$, 1,580.9 cm$^{-1}$, 1,604.3 cm$^{-1}$, 1,618.6 cm$^{-1}$, 1,633.2 cm$^{-1}$, 2,697.9 cm$^{-1}$, 2,842.7 cm$^{-1}$, 2,946.1 cm$^{-1}$, 3,005.3 cm$^{-1}$, and 3,066.4 cm$^{-1}$; and
   D) a crystal form designated as crystal form D, characterized in that, it has characteristic diffraction peaks at about 6.034, 8.699, 12.589, 18.108, 21.854, 24.224, 25.146 and 26.172° in an X-ray powder diffraction spectrum represented by Cu-Kα radiation and 2θ diffraction angle; two thermal absorption peaks at 131±3° C. and 190±3° C. respectively in a DSC thermogram; and characteristic infrared absorption peaks at 422.8 cm$^{-1}$, 454.3 cm$^{-1}$, 466.6 cm$^{-1}$, 505.6 cm$^{-1}$, 581.8 cm$^{-1}$, 617.7 cm$^{-1}$, 658.5 cm$^{-1}$, 739.3 cm$^{-1}$, 774.6 cm$^{-1}$, 820.3 cm$^{-1}$, 871.8 cm$^{-1}$, 892.6 cm$^{-1}$, 917.5 cm$^{-1}$, 962.6 cm$^{-1}$, 983.2 cm$^{-1}$, 999.7 cm$^{-1}$, 1,050.0 cm$^{-1}$, 1,067.8 cm$^{-1}$, 1,110.5 cm$^{-1}$, 1,140.5 cm$^{-1}$, 1,203.4 cm$^{-1}$, 1,244.5 cm$^{-1}$, 1,268.1 cm$^{-1}$, 1,293.8 cm$^{-1}$, 1,337.1 cm$^{-1}$, 1,363.8 cm$^{-1}$, 1,390.5 cm$^{-1}$, 1,455.5 cm$^{-1}$, 1,493.9 cm$^{-1}$, 1,515.6 cm$^{-1}$, 1,530.5 cm$^{-1}$, 1,567.2 cm$^{-1}$, 1,605.6 cm$^{-1}$, 1,638.0 cm$^{-1}$, 1,769.6 cm$^{-1}$, 2,726.3 cm$^{-1}$, 2,847.6 cm$^{-1}$, 2,945.2 cm$^{-1}$, 3,024.2 cm$^{-1}$, 3,065.1 cm$^{-1}$, 3,086.0 cm$^{-1}$, and 3,150.6 cm$^{-1}$.

2. A method for preparing the crystal foil is of demethyleneberberine hydrochloride according to claim 1, comprising the following steps:
   (1) adding 4 g of phloroglucinol into 100 ml of 40%-60% sulfuric acid, and stirring, so that the phloroglucinol is dissolved;
   (2) adding 5 g of berberine hydrochloride into the solution obtained in the step (1), and stirring for 2 h at 80° C.-100° C.;
   (3) adding the solution obtained in the step (2) into 100 ml of saturated salt solution, and stirring for 2 h;
   (4) filtering the mixed solution obtained in the step (3) by suction-filtration, dissolving filter cake with 100 ml of methanol in water bath at 70° C., and recrystallizing;
   (5) filtering the solution obtained in the step (4) by suction-filtration, dissolving filter cake with 100 ml of methanol in water bath at 70° C., recrystallizing, and performing suction-filtration;
   (6) drying a yellow solid obtained in the step (5) by vacuum drying for 24 h at room temperature, so that a crystal form B of demethyleneberberine hydrochloride is obtained;
   (7) filtering the solution obtained in the step (4) by suction-filtration, dissolving filter cake with 100 ml of ethanol in water bath at 80° C., recrystallizing, and performing suction-filtration;
   (8) drying a yellow solid obtained in the step (7) by vacuum drying for 24 h at room temperature, so that a crystal form C of demethyleneberberine hydrochloride is obtained;
   (9) filtering the solution obtained in the step (4) by suction-filtration, dissolving 1 g of filter cake with 12 ml of ethanol in water bath at 80° C. while stirring, performing suction-filtration and collecting filter cake;
   (10) drying a yellow solid obtained in the step (9) by vacuum drying for 24 h at room temperature, so that a crystal form A of demethyleneberberine hydrochloride is obtained;

(11) filtering the solution obtained in the step (4) by suction-filtration, dissolving 1 g of filter cake with 30 ml of deionized water in water bath at 74° C. while stirring, recrystallizing, and performing suction-filtration; and

(12) drying a yellow solid obtained in the step (11) by vacuum freeze-drying for 48 h, so that a crystal form D of demethyleneberberine hydrochloride is obtained.

3. The method for preparing the crystal forms of demethyleneberberine hydrochloride according to claim 2, wherein the step (5) further comprises: adding a small amount of seed crystals, adding 10-20 vol. % of diethyl ether, adding 10-20 vol. % of xylene, and adding 10-20 vol. % of toluene.

4. The method for preparing the crystal form of demethyleneberberine hydrochloride according to claim 2, wherein the step (7) further comprises: adding a small amount of seed crystals, adding 10-20 vol. % of diethyl ether, adding 10-20 vol. % of xylene, and adding 10-20 vol. % of toluene.

5. A pharmaceutical composition comprising crystal form A, B, C and/or D of demethyleneberberine hydrochloride according to claim 1.

6. The pharmaceutical composition, according to claim 5, formulated as a tablet, capsule, pill or as a sustained-release agent, or for injection, or as a microparticle administration system.

7. A method for treating liver fibrosis, acute and/or chronic alcoholic liver disease, ulcerative colitis, an immune liver injury and/or a nonalcoholic fatty liver disease, wherein said method comprises administering, to a subject in need of such treatment, a crystal form of demethyleneberberine hydrochloride according to claim 1.

8. A method for providing a hypoglycemic effect and/or for treating diabetes, wherein said method comprises administering, to a subject in need of such treatment, a crystal faun of demethyleneberberine hydrochloride according to claim 1.

* * * * *